United States Patent
Tets et al.

(10) Patent No.: US 9,757,413 B2
(45) Date of Patent: Sep. 12, 2017

(54) WEIGHT REDUCING COMPOSITION

(71) Applicants: Georgy Viktorovich Tets, St. Petersburg (RU); Viktor Veniaminovich Tets, St. Petersburg (RU)

(72) Inventors: Georgy Viktorovich Tets, St. Petersburg (RU); Viktor Veniaminovich Tets, St. Petersburg (RU)

(*) Notice: Subject to any disclaimer, the term of this patent is extended or adjusted under 35 U.S.C. 154(b) by 0 days.

(21) Appl. No.: 14/957,802

(22) Filed: Dec. 3, 2015

(65) Prior Publication Data

US 2016/0082041 A1    Mar. 24, 2016

Related U.S. Application Data

(62) Division of application No. 12/443,043, filed as application No. PCT/RU2006/000501 on Sep. 26, 2006, now Pat. No. 9,205,072.

(51) Int. Cl.

| | |
|---|---|
| A61K 33/06 | (2006.01) |
| A23L 2/52 | (2006.01) |
| A61K 31/194 | (2006.01) |
| A61K 31/337 | (2006.01) |
| A61K 31/375 | (2006.01) |
| A61K 33/00 | (2006.01) |
| A61K 33/24 | (2006.01) |
| A61K 36/38 | (2006.01) |
| A61K 36/515 | (2006.01) |
| A61K 36/752 | (2006.01) |
| A61K 36/82 | (2006.01) |
| A61K 36/886 | (2006.01) |
| A61K 36/9066 | (2006.01) |
| A61K 45/06 | (2006.01) |
| A23L 33/16 | (2016.01) |

(52) U.S. Cl.
CPC ............... *A61K 33/06* (2013.01); *A23L 2/52* (2013.01); *A23L 33/16* (2016.08); *A61K 31/194* (2013.01); *A61K 31/337* (2013.01); *A61K 31/375* (2013.01); *A61K 33/00* (2013.01); *A61K 33/24* (2013.01); *A61K 36/38* (2013.01); *A61K 36/515* (2013.01); *A61K 36/752* (2013.01); *A61K 36/82* (2013.01); *A61K 36/886* (2013.01); *A61K 36/9066* (2013.01); *A61K 45/06* (2013.01); *A23V 2002/00* (2013.01)

(58) Field of Classification Search
CPC .. A61K 33/00; A61K 33/06; A23V 2250/154; A23V 2250/156; A23V 2250/1612; A23V 2250/1614
See application file for complete search history.

(56) References Cited

U.S. PATENT DOCUMENTS

2005/0106273 A1    5/2005  Peyman
2008/0118577 A1    5/2008  Moritani et al.

FOREIGN PATENT DOCUMENTS

| CN | 1593254 A | 3/2005 |
|---|---|---|
| KZ | 13953 A | 2/2004 |
| RU | 2137405 C1 | 9/1999 |
| RU | 2192153 C2 | 11/2002 |
| RU | 2221462 C1 | 1/2004 |
| WO | 2005/107775 A1 | 11/2005 |

OTHER PUBLICATIONS

Azoulay et al., Comparison of the Mineral Content of Tap Water and Bottled Waters, 2001, J Gen Intern Med, vol. 16, pp. 168-175.*
Marx et al., Magnesium in Drinking Water and Ischemic Heart Disease, 1997, Epidemiologic Reviews, vol. 19 No. 2, pp. 258-272.*
Azoulay et al., Comparison of the Mineral Content of Tap Water and Bottled Waters, Mar. 2001, Journal Gen Intern Med, vol. 16, pp. 168-175.
Boyles, Drinking Water May Speed Weight loss, Jan. 5, 2004, webmed, pp. 1-2.
Garzon et al. "Variation in the mineral content of commercially available bottled waters: implications for health and disease", Aug. 1998, The American Journal of Medicine, vol. 105 iss. 2, pp. 125-130.
International Search Report dated May 3, 2007, from corresponding International Application No. PCT/RU2006/000501.
Translation of the International Preliminary Report on Patentability dated Jun. 29, 2009, from corresponding Application No. PCT/RU2006/000501.
"Kniga o mineralnoi vode", Moskva, Veche, 1998, pp. 38, 79, 83, 121-122 ("The book is about the mineral water", Moscow, Veche, 1998, pp. 38, 79, 83, 121-122).
Product specification for Natural Mineral Table and Therapeutic Water "Novoterskaya", TU9185-003-36800549-02, 2006.
Product specification for Natural mineral Table and Therapeutic Water "Essentuki #4 well 49", TU 9185-001-50243825-03, 2009.
Product specification for Spring Water "Rosinka-2", TU 9185-001-05126800-97, 1997.
Product description for "Zolotoy rodnik" (Gold spring)—mineral table water in polyethylene bottles, 1.5 L, 2001, http://www.water-dp.com.ua/products/mineral.htm.
Product description for Donat Mg, 2003, http://www.donatmg.net/en.

* cited by examiner

*Primary Examiner* — Ali Soroush
(74) *Attorney, Agent, or Firm* — Troutman Sanders LLP

(57) ABSTRACT

The invention relates to soft drink industry, in particular, to dietetic nutrition. The inventive weight reducing composition comprises 0.01-10 mg/l of sodium and 25-150 mg/l of magnesium, the rest being water. Said composition (drinking water) makes it possible to reduce weight without altering the usual eating habits. In addition, consumption of said drinking water results in reduction of weight by 1.2-2.9 kg.

14 Claims, No Drawings

WEIGHT REDUCING COMPOSITION

The present application is a divisional of U.S. patent application Ser. No. 12/443,043, filed Mar. 26, 2009, which is the U.S. National Phase of International Patent Application Serial No. PCT/RU2006/000501, filed Sep. 26, 2006. The contents of the foregoing applications are hereby incorporated by reference in their entireties.

TECHNICAL FIELD

The invention relates to dietetic nutrition and can be used for reducing weight (weight loss).

BACKGROUND ART

The overweight problem is among the most pressing issues of the present day dietetics. More than 20% of the population suffers from various degrees of obesity, whereas for adult population aged over 40 years the overweight is a problem for more than 40%.

Today most treatments for overweight people that do not involve is consultations with medical specialists consist mainly in modifying the diet and increasing physical exercise. The low energy diet (1200-1300 calories per day) is considered to be the most effective one, providing reduction of body weight by 6-7 kg within 6 months; however, the quantitative and qualitative restrictions on the food, as well as the need for certain changes in the eating habits and the daily routine, make the utilization of this technique rather difficult. Most patients that follow diets for a long time eventually go back to their usual eating habits, whereupon they gain back all of the lost weight.

Sibutramine, leptin and cholecystokinin are among the known drugs that influence the hunger centre in brain and lower the appetite. These drugs must be used under medical supervision due to high risk of such side effects as allergies, hypertension, tachycardia, etc.

Drugs that prevent absorption of fats in the intestine are also wide known and include biguanide derivatives, orlistat [see Encyclopedia of Drugs, edition 7, 2000, p. 475] and various herbal infusions. Orlistat inhibits intestinal lipase, thus blocking the breaking down of triglycerides in the intestine and reducing the absorption of free fatty acids and monoglycerides. Use of such drugs is almost always accompanied by diarrhoea, urgent bowel movements and fecal incontinence, resulting in significant inconveniences for the patients.

It is a known fact that everyday intake of water is essential for humans. An adult individual must drink 2.0-2.5 litres of water every day. Water plays an important part in physiological processes of maintaining and/or changing the body mass. For example, fat is known to break down only in the presence of water. On the other hand, retention of water in the organism not only results in increased body mass and edemas, but can also increase the formation of fat deposits.

Due to the important hygienic role of water, its quality is rigorously standardized and controlled. Different countries set their own principal hygienic standards for drinking water, which are based on similar values (see Table 1).

Water from various natural sources contains mineral salts that define its taste as well as the therapeutic properties. Unlike therapeutic water, table water usually has low mineral content. Purified and then remineralized water is also popular. As a rule, such water falls into the table water category and is not intended for use in treatment or prevention of overweight.

A known composition comprises (mg/l):

| | |
|---|---|
| Bicarbonate $HCO_3$ | 1000-1200 |
| Sulfate $SO_4$ | 900-1700 |
| Chloride Cl | 300-500 |
| Calcium Ca | 300-400 |
| Magnesium Mg | <100 |
| Sodium + Potassium (Na + K) | 700-1200 |
| Silicic acid $H_2SiO_3$ | 30-90 |
| Mineral content | 3.2-5.8 g/l | see "therapeutic mineral table water Novoterskaya Tselebnaya", TU9185-003-36800549-02. This water is recommended, in particular, for obese people. However, a very high content of sodium and undefined minimal amount of magnesium make this composition inefficient in treating the overweight problem; the water does not have any noticeable spasmolytic effect that would suppress hunger and increase the peristalsis and lipolysis. Hunger spasms play an important part in creating the sense of hunger, because they are perceived by the individual as the demand for food.

Another known water, "natural mineral water Essentuki No. 4", TU 9185-001-50243825-03, recommended for reducing the overweight problem, comprises (mg/l):

| | |
|---|---|
| Bicarbonate $HCO_3$ | 3900-4900 |
| Sulfate SO4 | <100 |
| Chloride Cl | 600-800 |
| Calcium Ca | <100 |
| Magnesium Mg | <75 |
| Sodium + Potassium (Na + K) | 1700-2700 |

This mineral water has the same disadvantages as Novoterskaya Tselebnaya water.

The content of the "therapeutic natural table water Rosinka", TU-9185-001-05126800-97, is the closest one to the inventive engineering solution and comprises (mg/l):

| | |
|---|---|
| Bicarbonate $HCO_3$ | 100-200 |
| Sulfate $SO_4$ | <30 |
| Chloride Cl | <80 |
| Calcium Ca | <20 |
| Magnesium Mg | <25 |
| Sodium + Potassium (Na + K) | <30 |
| Mineral content | 0.3 g/l |

The applicant performed analysis of the content of sodium and magnesium in 12 samples (12 bottles of Rosinka that were purchased in different sales points in St. Petersburg and Moscow). The results showed that the content of sodium in the samples varied from 24 to 35 mg/l, while the content of magnesium varied from 16 to 20 mg/l. However, as it was noted above, increased content of sodium causes retention of water in the organism; also this composition does not provide a noticeable spasmolytic effect.

Due to the abovementioned disadvantages, the "therapeutic natural table water Rosinka" has low efficiency in overweight treatment.

SUMMARY OF THE INVENTION

It is an object of the present invention to provide a weight reducing composition that would efficiently aid in reduction of extra weight due to its ratio of ingredients.

According to the invention there is provided a weight reducing composition comprising cations of sodium, magnesium and water, wherein said components are included according to the following ratio:

| Na+ | 0.01-10 mg/l |
| Mg++ | 25-150 mg/l |
| H$_2$O | the rest. |

Anions are not so very important.

The applicant has not found any sources of information containing data on engineering solutions identical to the present invention. In applicant's opinion, this enables to conclude that the invention conforms to the criterion "Novelty" (N).

While analyzing the inventive engineering solution for conformance to the criterion "Inventive Step", the applicant discovered a novel effect that had not been previously mentioned in any other sources, namely that magnesium has a pronounced spasmolytic effect on the stomach only under low concentrations of sodium, wherein the concentration of magnesium should be at least 2.5 mg/l; the intake of water causes irritation of mechanoreceptors of the stomach wall and secretion of cholecystokinin by I-cells of the duodenum, with subsequent transfer of impulses to the hunger center in hypothalamus and to the limbic system in the brain; this results in reduced secretion of gastric and intestinal juices, reduced absorption of nutrients, decreased feeling of hunger, increased peristalsis, intensified lipolysis; for this, the concentration of sodium must not exceed 10 mg/l (sodium concentrations below 0.01 mg/l are technically difficult to achieve). When the concentration of sodium exceeds 10 mg/l, the spasmolytic effect is not pronounced, even with magnesium concentrations above 25 mg/l. The effect is also absent for sodium concentrations below 10 mg/l if the concentration of magnesium is below 25 mg/l.

Therefore, a pronounced spasmolytic effect can be obtained only when concentration of sodium is not higher than 10 mg/l and the concentration of magnesium is between 25 and 150 mg/l (magnesium content above 150 mg/l is not recommended due to purgative side effects.)

The applicant has not found any sources of information containing data on the influence of the inventive novel features on the technical result produced through realization of said features. In applicant's opinion, this enables to conclude that the present engineering solution conforms to the criterion "Inventive Step" (IS).

BRIEF DESCRIPTION OF THE DRAWINGS

The invention is further explained, by way of example, without reference to any drawings.

PREFERRED EMBODIMENT

Utilization of the inventive composition is further illustrated by means of the following examples.

EXAMPLE 1

The participants of the experiment—10 volunteers aged 20-39 yrs—received the weight reducing composition comprising 0.01 mg/l of sodium and 25 mg/l of magnesium, the rest being water, at room temperature. The participants drank this water during 30 days, twice a day, 5-10 minutes before the meal (before dinner and supper), in the amount of 150 ml. Their eating habits, diet, daily routine and physical exercise level remained the same as before the experiment. All participants were overweight according to the Body Mass Index (27.0-35.6 kg/m$^2$), which is calculated by dividing body weight in kilograms by the square of the individual's height in meters. For individuals with normal weight this parameter ranges from 18.5 to 24.9 kg/m$^2$. Results of the experiment are shown in Table 2.

EXAMPLE 2

The participants of the experiment 8 volunteers aged 20-39 yrs—received the weight reducing composition comprising 5.0 mg/l of sodium and 50 mg/l of magnesium, the rest being water, at room temperature. The participants drank this water during 30 days, twice a day. 5-10 minutes before the meal (before dinner and supper), in the amount of 150 ml. Their eating habits, diet, daily routine and physical exercise level remained the same as before the experiment. All participants were overweight according to the Body Mass Index (27.0-35.6 kg/m$^2$), which is calculated by dividing body weight in kilograms by the square of the individual's height in meters. For individuals with normal weight this parameter ranges from 18.5 to 24.9 kg/m$^2$. Results of the experiment are shown in Table 3.

EXAMPLE 3

The participants of the experiment—10 volunteers aged 20-39 yrs—received the weight reducing composition comprising 10 mg/l of sodium and 150 mg/l of magnesium, the rest being water, at room temperature. The participants drank this water during 30 days, twice a day, 5-10 minutes before the meal (before dinner and supper), in the amount of 150 ml. Their eating habits, diet, daily routine and physical exercise level remained the same as before the experiment. All participants were overweight according to the Body Mass Index (27.0-35.6 kg/m$^2$), which is calculated by dividing body weight in kilograms by the square of the individual's height in meters. For individuals with normal weight this parameter ranges from 18.5 to 24.9 kg/m$^2$. Results of the experiment are shown in Table 4.

EXAMPLE 4

The participants of the experiment—9 volunteers aged 20-39 yrs—received the weight reducing composition comprising 25 mg/l of sodium and 50 mg/l of magnesium, the rest being water, at room temperature. The participants drank this water during 30 days, twice a day, 5-10 minutes before the meal (before dinner and supper), in the amount of 150 ml. Their eating habits, diet, daily routine and physical exercise level remained the same as before the experiment. All participants were overweight according to the Body Mass Index (27.0-35.6 kg/m$^2$), which is calculated by dividing body weight in kilograms by the square of the individual's height in meters. For individuals with normal weight this parameter ranges from 18.5 to 24.9 kg/m$^2$. Results of the experiment are shown in Table 5.

This example shows that there were no statistically significant reduction of body weight (at least 1 kg after 30 days), even though the water contained sufficient amount of magnesium—the reason for this was high concentration of sodium.

EXAMPLE 5

The participants of the experiment—9 volunteers aged 20-39 yrs—received the weight reducing composition comprising 1 mg/l of sodium and 10 mg/l of magnesium, the rest being water, at room temperature.

The participants drank this water during 30 days, twice a day, 5-10 minutes before the meal (before dinner and supper), in the amount of 150 ml. Their eating habits, diet, daily routine and physical exercise level remained the same as before the experiment. All participants were overweight according to the Body Mass Index (27.0-35.6 kg/m$^2$), which is calculated by dividing body weight in kilograms by the square of the individual's height in meters. For individuals with normal weight this parameter ranges from 18.5 to 24.9 kg/m$^2$. Results of the experiment are shown in Table 6.

This example shows that even very low concentrations of sodium, when combined with insufficient concentration of magnesium, do not provide a significant reduction of body weight.

EXAMPLE 6

The participants of the experiment—10 volunteers aged 20-39 yrs—received the "therapeutic natural table water Rosinka", comprising less than 30 mg/l of sodium+potassium and less than 30 mg/l of magnesium, the rest being water, at room temperature. The participants drank this water during 30 days, twice a day, 5-10 minutes before the meal (before dinner and supper), in the amount of 150 ml. Their eating habits, diet, daily routine and physical exercise level remained the same as before the experiment. All participants were overweight according to the Body Mass Index (27.0-35.6 kg/m$^2$), which is calculated by dividing body weight in kilograms by the square of the individual's height in meters. For individuals with normal weight this parameter ranges from 18.5 to 24.9 kg/m$^2$. Results of the experiment are shown in Table 7.

EXAMPLE 7

The participants of the experiment—10 volunteers aged 20-39 yrs—received the "natural mineral water Essentuki No. 4", comprising 1700-2700 mg/l of sodium+potassium and less than 75 mg/l of magnesium, the rest being water, at room temperature. The participants drank this water during 30 days, twice a day, 5-10 minutes before the meal (before dinner and supper), in the amount of 150 ml. Their eating habits, diet, daily routine and physical exercise level remained the same as before the experiment. All participants were overweight according to the Body Mass Index (27.0-35.6 kg/m$^2$), which is calculated by dividing body weight in kilograms by the square of the individual's height in meters. For individuals with normal weight this parameter ranges from 18.5 to 24.9 kg/m$^2$. Results of the experiment are shown in Table 8.

The abovementioned examples show that the inventive composition provides a twofold or even threefold increase in efficiency in comparison with the known compositions (Rosinka, Essentuki No. 4, Novoterskaya Tselebnaya) that are recommended as weight-reducing treatment for overweight people.

Water-soluble vitamins can be added to the inventive composition, for example, ascorbic acid or B vitamins; also, one may add extracts or infusions of green tea, aloe, garcinia, gentiana, corn silk, turmeric, grapefruit, citric acid, etc.

INDUSTRIAL APPLICABILITY

The realization of the invention is done by means of common materials and factory equipment. In applicant's opinion, this enables to conclude that the invention conforms to the criterion "Industrial Applicability" (IA).

Principal Hygienic Standards

TABLE 1

| Parameter | Unit | WHO* | USEPA** | EU*** | RF SanPiN**** |
|---|---|---|---|---|---|
| PH | pH units | | 6.5-8.5 | 6.5-8.5 | 6-9 |
| Total mineral content | mg/l | <1000 | <500 | <1500 | <1000 |
| Total hardness | mmol/l | | | <1.2 | <7.0 |

*World Health Organization, Guidelines for Drinking-Water Quality, 1984 (revised and updated in 1992).
**U.S. Environment Protection Agency, National Primary Drinking Water Regulations.
***Directive of the European Community (EC) regarding the quality of water intended for human consumption (80/778/EC) was approved by the European Council on 15 Jul. 1980.
****Sanitary Regulations and Standards of Russian Federation (SanPiN);

(SanPiN 2.1.4.559-96) "Drinking water. Hygienic requirements to the quality of water in centralized systems of drinking water supply. Quality control" were approved by Resolution of Goskomsanepidnadzor RF (State Committee on Sanitary and Epidemiology Surveillance) of 24 October 1996 and put into effect on 1 Jul. 1997.

Results of the Experiment of Example 1

TABLE 2

| Content of the composition | Reduction of body weight among the participants (in kg) after 30 days |
|---|---|
| Sodium - 0.01 mg/l, magnesium - 25 mg/l, water - the rest. | 1.30 +/- 0.2 |

Results of the Experiment of Example 2

TABLE 3

| Content of the composition | Reduction of body weight among the participants (in kg) after 30 days |
|---|---|
| Sodium - 5.0 mg/l, magnesium - 50 mg/l, water - the rest. | 1.70 +/- 0.25 |

Results of the Experiment of Example 3

TABLE 4

| Content of the composition | Reduction of body weight among the participants (in kg) after 30 days |
|---|---|
| Sodium - 10 mg/l, magnesium - 150 mg/l, water - the rest. | 1.40 +/- 0.3 |

Results of the Experiment of Example 4

TABLE 5

| Content of the composition | Reduction of body weight among the participants (in kg) after 30 days |
|---|---|
| Sodium - 25 mg/l, magnesium - 50 mg/l, water - the rest. | 0.5 +/− 0.1 |

Results of the Experiment of Example 5

TABLE 6

| Content of the composition | Reduction of body weight among the participants (in kg) after 30 days |
|---|---|
| Sodium - 1 mg/l, magnesium - 10 mg/l, water - the rest. | 0.4 +/− 0.2 |

Results of the Experiment of Example 6

TABLE 7

| Content of the "therapeutic natural table water Rosinka" | Reduction of body weight among the participants (in kg) after 30 days |
|---|---|
| Sodium + potassium - less than 30 mg/l, magnesium - less than 30 mg/l, water - the rest. | 0.55 +/− 0.15 |

Results of the Experiment of Example 7

TABLE 8

| Content of the "natural mineral water Essentuki No. 4" | Reduction of body weight among the participants (in kg) after 30 days |
|---|---|
| Sodium + potassium - 1700-2700 mg/l, magnesium - less than 75 mg/l, water - the rest. | 0.50 +/− 0.3 |

The invention claimed is:

1. A water composition consisting essentially of:
0.01-10 mg/l sodium;
25-150 mg/l magnesium; and
water.

2. The water composition of claim 1, further comprising an additive selected from the group consisting of: ascorbic acid; B vitamins; extracts or infusions of green tea; aloe; garcinia; gentiana; corn silk; turmeric; grapefruit; and citric acid.

3. The water composition of claim 1, wherein said sodium is a sodium cation.

4. The water composition of claim 1, wherein said sodium is a sodium salt.

5. The water composition of claim 1, wherein said magnesium is a magnesium cation.

6. The water composition of claim 1, wherein said magnesium is a magnesium salt.

7. The water composition of claim 1, wherein said composition is essentially free of any cation other than sodium and magnesium.

8. The water composition of claim 1, wherein said composition is at room temperature.

9. A water composition consisting of:
0.01-10 mg/l sodium;
25-150 mg/l magnesium; and
water.

10. The water composition of claim 9, wherein said sodium is a sodium cation.

11. The water composition of claim 9, wherein said sodium is a sodium salt.

12. The water composition of claim 9, wherein said magnesium is a magnesium cation.

13. The water composition of claim 9, wherein said magnesium is a magnesium salt.

14. The water composition of claim 9, wherein said composition is at room temperature.

* * * * *